United States Patent
Morgan

[11] Patent Number: 6,016,727
[45] Date of Patent: Jan. 25, 2000

[54] RECESS DRIVE BONE SCREW AND COOPERABLE DRIVING TOOL

[75] Inventor: Frank H. Morgan, Las Vegas, Nev.

[73] Assignee: Sofamor Danek Properties, Inc., Memphis, Tenn.

[21] Appl. No.: 09/217,108

[22] Filed: Dec. 21, 1998

Related U.S. Application Data

[63] Continuation of application No. 08/810,306, Feb. 28, 1997, abandoned.

[51] Int. Cl.[7] .................................................... B25B 15/00
[52] U.S. Cl. ............................... 81/436; 411/403; 606/73; 81/461
[58] Field of Search ...................... 81/436, 461; 411/403; 606/72, 73

[56] References Cited

U.S. PATENT DOCUMENTS

| | | |
|---|---|---|
| 1,875,484 | 9/1932 | Nigra . |
| 2,066,132 | 12/1936 | Zihler . |
| 2,268,515 | 12/1941 | Olson . |
| 2,285,461 | 6/1942 | Purtell . |
| 3,584,667 | 6/1971 | Reiland . |
| 3,952,618 | 4/1976 | Seamon . |
| 4,269,246 | 5/1981 | Larson et al. . |
| 5,019,080 | 5/1991 | Hemer . |
| 5,105,690 | 4/1992 | Lazzara et al. . |
| 5,171,117 | 12/1992 | Seidl . |
| 5,300,076 | 4/1994 | Leriche . |
| 5,743,914 | 4/1998 | Skiba ......................................... 606/73 |

FOREIGN PATENT DOCUMENTS

| | | |
|---|---|---|
| 0 458 449 A1 | 11/1991 | European Pat. Off. . |
| 2 201 645 | 4/1974 | France . |
| 914240 | 6/1954 | Germany . |
| 43 21 325 | 1/1995 | Germany . |
| 296 11 140 U | 9/1996 | Germany . |
| 1 534 414 | 12/1978 | South Africa . |
| WO 90 01399 | 2/1990 | WIPO . |
| WO 92 20306 | 11/1992 | WIPO . |

OTHER PUBLICATIONS

K. Schnider: "Dreherei Und Chirurgie" *ZWF Zeitschrift Fur Wirtschaftliche Fertigung Und Automatisierung* vol. 4 No. 8, Aug. 1,1989, pp. S28.

"Compact CD Low Back" *Explanatory Document for Instrument Nurses,* publication by Sofamor Spine Division, p. 53.

Synthes Maxillofaciall Catalog, pp. 76–77, 1989.

"Leibinger COM/MAND Comprehensive Mandibular Fixation System", 5 pp., 1994.

*Primary Examiner*—James G. Smith
*Attorney, Agent, or Firm*—Woodard, Emhardt, Naughton, Moriarty & McNett, Patent And Trademark Attorneys

[57] ABSTRACT

A fastener with a recessed drive socket and a driving tool with a cooperable driving head. The socket having a cylindrical interior wall interrupted by a plurality of driving corners. The driver having a tapered driving head including a plurality of sharpened driving edges adapted to engage the driving corners. The tapered driving end may be axially forced into the driving socket such that the plurality of driving edges frictionally engage the driving corners to hold the fastener on the driver and to enhance torque transmission. The cylindrical walls of the socket and the walls of the driver bit between the driving edges cooperate to define a fluid channel for passage of fluid around the driving head during positioning within the socket.

21 Claims, 5 Drawing Sheets

RECESS DRIVE BONE SCREW AND COOPERABLE DRIVING TOOL

CROSS-REFERENCE TO RELATED APPLICATIONS

The present application is a continuation of U.S. application Ser. No. 08/810,306 filed on Feb. 28, 1997 now abandoned, which is hereby incorporated by reference in its entirety.

BACKGROUND OF THE INVENTION

The present invention relates broadly to a fastener drive system and cooperable driving tool. More specifically, the present invention relates to a fastener drive system for applications where the presence of fluid, such as in the attachment of a medical prosthesis to bone, in a very small clearance gap between the driver and the fastener may result in the generation of hydraulic forces inhibiting free movement of the driver with respect to the fastener.

Medical prosthetic arts have advanced substantially in both design and the materials used to create prosthetics. Typically, a combination of mechanical fasteners and adhesives are used to secure a prosthesis to surrounding bone. A high degree of precision is required in order to securely retain the prosthesis in a proper working position. When the prosthesis is fitted to surrounding bone it is preferred to make the prosthesis fit correctly the first time to avoid having to make adjustments. Correct placement of the fastener is particularly important in craniomaxillofacial surgeries where a very small fastener must be placed in a precise location.

The treatment of fractures of the craniomaxillofacial region proceeds by reducing the fractured bones to their anatomically correct positions, and there fixing the bones in place. One common way to fix the bone fragments in place is by the technique of mini-plate fixation. The mini-plate is held in place by a series of small bone screws extending through the plate and into the bone. Typically, these screws are very small with an outer thread diameter ranging from 1.0 mm to 5.0 mm.

In many surgical applications, the placement of the screw is limited to a precise location either by the anatomical structure or because of the size of the fragment to be fixed. Moreover, the bone at the site of fixation is often relatively thin, particularly in children, thus increasing the risk of screw pull out. Should fluid enter the recess of either the driver or the fastener, there is a potential for the bone screw to strip the bone holding the screw as a result of hydraulic forces generated by the trapped fluid which acts to hold the driver within the socket.

In the field of orthopedics, fasteners and drivers of various types have long been employed to transmit rotational force from the driver to the fastener. One of the simplest fastener-driver combination is a slotted recess in the fastener head. Other drive forms include a slot with a center alignment hole, crucifrom, phillips, square, hexagon, and hexalobe. Each of these designs offers desirable features either in ease of manufacture or reliable torque transmission. For each of these drive systems, the geometric configuration utilized by the fastener drive area is repeated in the drive end of the driver with only slightly different dimensions to allow sufficient clearance to be slideably received therein.

In an effort to increase torque transmission and limit camming out during the torque transmission procedure, the tolerances between the driver end and the fastener driving area have continued to be reduced. Moreover, as disclosed in European Patent Publication 0,458,449 in some applications the drive end includes a spacer element to ensure secure engagement of the driver with the socket. Still further, U.S. Pat. No. 4,269,246 discloses that it is desirable that the driver head have a taper to encourage all of the surfaces of the driver to securely engage the surfaces of the socket, thereby increasing the frictional fit between the socket and driver.

As the need for smaller screws and other miniature fasteners have developed, particularly in the medical field, so to have the manufacturing tolerances necessary to provide a secure match between the driving tool and the fasteners recessed driving socket. While the tolerances utilized in small screws, i.e. often with a thread diameter less than 5 mm, has been effective to provide the desired torque transmission capacity, another relatively unexpected problem has developed.

Very tight tolerances required to manufacture small fasteners provide very little clearance between the driver and the drive area of the fastener. Any fluid trapped in these tight areas may generate hydraulic forces which can inhibit movement of the driver within the drive area. The probability that fluid will enter the driving engagement is increased when used in medical procedures were bodily fluids, irrigation fluids, and other fluids are routinely present. This creates a problem because the driving tool may not be fully seated in the socket and therefore may have a tendency to cam out of the socket or to allow stripping of the fastener driving area and/or dulling of the driving tool. This problem is intensified by having very small screws and driving tools were the amount of metal to resist the torque exerted when inserting the screw is extremely small. Thus there is a greater potential for stripping of the socket or dulling of the driving tool if the tool is not properly seated to take advantage of the entire driving surfaces of the socket.

Another problem related to the short coming discussed above, is that even if enough force can be applied to overcome the hydraulic forces and properly seat the driver in the socket, the driver may be locked into the socket by hydraulic forces resulting from the fluid held between the driver and the socket. Essentially, the surface tension of any fluid at the bottom of the socket and disposed between the driving tool and walls of the socket hydraulically holds the driving tool in place. Because of the close tolerances between the driving tool and socket side walls the fluid cannot readily move to allow air or some other fluid to enter and relieve the hydraulic lock. As a result an exceptional amount of axial force must be applied to the driver to remove it from the fastener.

In the case of small screws, particularly those placed in relatively soft material (i.e. bone), the force applied to remove the driver can over come the purchase of the screw in the receiving material. This is especially troublesome in medical procedures where there may only be a single location for a bone screw to be placed. In these instances, pull out of the original bone screw strips the hole and may require the use of bone cement or a larger diameter screw to be used.

A need therefore exists for a fastener driving socket and cooperable driving tool which provide a channel for the passage of fluid upon engagement and disengagement of the driver with the fastener. Such a driving socket and cooperable driving tool must also provide effective torque transmission.

SUMMARY OF THE INVENTION

One form of the present invention contemplates a driver head for transmitting rotational force to a driving socket having a plurality of driving corners, the driver head having a longitudinal axis, the driver head comprising an external surface defining a plurality of driving edges extending substantially along the longitudinal axis and positioned to matingly engage the driving corners of the driving socket, the external surface further including a recessed portion between adjacent driving edges.

Another form of the invention contemplates a recessed drive socket for receiving a partially mating, rotational drive tool therein, the socket comprising a socket cavity having a generally cylindrical wall, the cylindrical wall interrupted by a plurality of driving corners, wherein the driving corners receive a portion of the driver tool therein.

Still another form of the invention contemplates a fastener and driver combination, comprising a fastener having a drive socket, the socket having a plurality of driving corners, and a driver having a driving head including a plurality of driving edges sized for mating engagement with corresponding driving corners of the fastener, the driving head further defining a recessed area between each driving edge.

Yet another form of the invention contemplates a fastener and driver combination, comprising a fastener having a recessed drive socket, the socket defined by a substantially cylindrical interior wall, the interior wall interrupted by a plurality of driving corners, and a driver having a driving head including an outer surface defining a plurality of driving edges spaced for mating engagement with the corresponding driving corners of the fastener, wherein upon engagement of the driving edges with the driving corners, the cylindrical interior wall of the fastener and the outer surface of the driver define at least one fluid channel, the fluid channel permitting the passage of fluid during movement of the driver with respect to the recessed drive socket.

Additionally, the invention includes a method for forming a recessed driving socket, comprising the steps of providing appropriately sized bar stock having a longitudinal axis, drilling a pilot hole into the bar stock aligned with the longitudinal axis thereby forming a cylindrical wall, and punching a plurality of driving corners into the cylindrical wall of the pilot hole leaving the curved walls of the pilot hole intact between adjacent driving corners.

A general object is to provide a fastener which is securely retainable on a driver.

Another general object is to provide a drive socket and driver which permit the expulsion of fluid from the socket as the driver is inserted.

A more specific object of the present invention is to provide a drive socket having a substantially cylindrical interior surface interrupted by a plurality of driving corners. The cylindrical surface defining a fluid channel for passage of fluid out of the socket when mated with a driving tool.

A further object of the present invention is to provide a driving tool with a driving head having a plurality of driving edges. The driving edges engaging a drive socket to hold it on the fastener and to provide enhanced torque transmission characteristics.

An additional object of the present invention is to provide a fastener and driver system with a plurality of tapering driving edges composed of a hardened material and upon insertion into a cooperable socket the edges slightly deform the driving corners composed of a relatively soft material. The deformation resulting in increased frictional engagement between the driving corners and the driving edges as well as increased torque transmission characteristics.

Still a further object of the present invention is to provide a method for making the socket and driver.

Related objects and advantages of the present invention will be apparent from the following description.

BRIEF DESCRIPTION OF THE DRAWINGS

FIG. 8(*a*) is an enlarged detail of two of the drive edges positioned in driving corners of the drive socket.

FIG. 8(*b*) is an enlarged detail of two of the drive edges deformably engaging driving corners of the drive socket.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Various configurations of drive sockets and mating drivers are well known in the art. Many of these configurations have been adapted for use in the medical arts, particularly in the area of orthopedic implants. However, the present invention presents a unique and non-obvious drive socket and companion driver providing secure frictional engagement, reliable torque transmission and a channel for passage of irrigation fluids, bodily fluids or any other fluids disposed between the drive socket and driver head.

Figure 1:
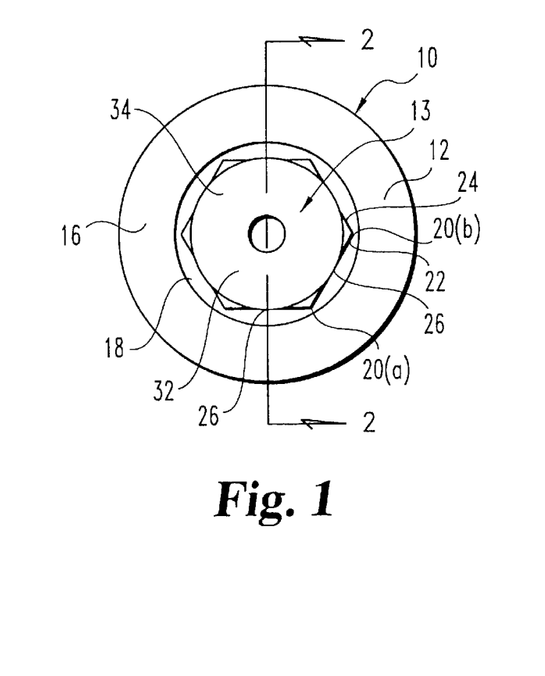
FIG. 1 is a top view of a recessed drive fastener according to the present invention.
Figure 2:
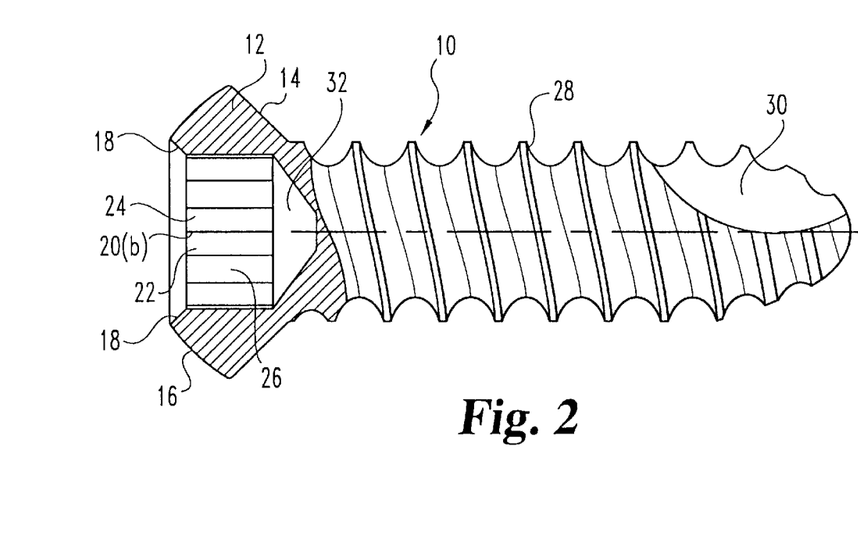
FIG. 2 is a partial cross-sectional view of the recessed drive fastener of FIG. 1 taken along section lines 2—2.
Figure 3:
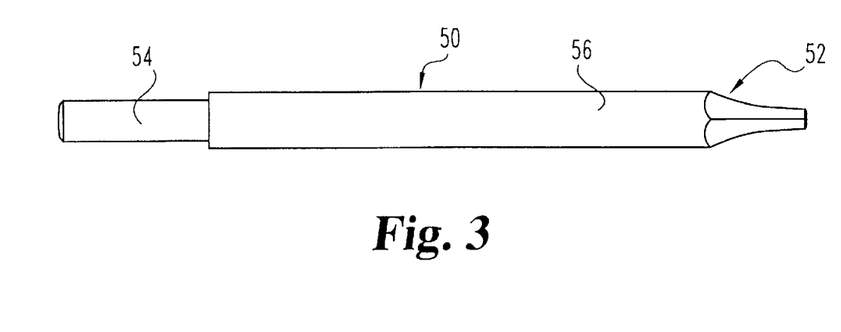
FIG. 3 is a driving tool cooperable with the recessed drive fastener of FIG. 1.

Referring now to the drawings, FIGS. 1 and 2 illustrate a drive socket according to the present invention mounted on a fastener. Fastener 10 has an enlarged driving head 12 defining drive socket 13 therein. In the preferred embodiment, enlarged fastener head 12 further includes a lower chamfered surface 14 adjacent threads 28 angled to mate with a correspondingly chamfered surface in a bone plate opening (not shown) to be anchored by fastener 10. Fastener head 12 also includes an upper chamfered surface 16 to reduce sharp edges which might adversely affect tissue overlying the head after insertion. Extending between chamfered surface 16 and drive socket 13 is internal chamfered surface 18. As will be understood by those skilled in the art, this chamfered surface assists the user in guiding a driving tool into the drive socket. Additionally, fastener 10, according to the preferred embodiment, has a divot 30 removed from the threaded shaft to permit the screw to be inserted in a self-tapping manner.

Although the fastener of the preferred embodiment is shown as a self-tapping bone screw, it will be understood that it could also be used with a previously tapped hole. Such a bone screw, substantially enlarged in the figures, typically has an outer thread diameter between 1.0 mm and 5.0 mm making it ideally suited for use in craniomaxillofacial procedures. Moreover, while a bone screw is shown, it is contemplated that the invention as described herein could be utilized with any number of internal drive fasteners and the illustration of a bone screw is provided for the purposes of illustration and not limitation.

Turning now more specifically to the present invention, drive socket 13 is defined by substantially cylindrical side wall 26 and bottom wall 32. Cylindrical side wall 26 is interrupted by a plurality of recessed driving corners 20. Preferably, each driving corner is formed by the junction of a pair of substantially planar side walls. Specifically, driving corner 20(b) is formed by the junction of substantially planar side walls 22 and 24. In the preferred embodiment cylindrical side wall 26 and driving corners 20 extend longitudinally essentially parallel to the longitudinal axis of the screw. Thus, in the preferred embodiment, the socket does not have a taper. However, it is contemplated that the socket may be tapered or that the driver corners may have a slight twist as they extend along the longitudinal axis.

In the preferred embodiment, drive socket 13 is formed by first drilling a pilot hole 34 into fastener head 12 to define cylindrical wall 26. Pilot hole 34 terminates in a chamfered bottom wall 32. After the pilot hole of the desired diameter has been drilled, driving corners 20 are punched into cylindrical wall 26 of pilot hole 34 in an equally spaced manner around its circumference. It will be understood that this procedure removes less material from the socket walls than the formation of a standard hexagonal drive. Thus, the formation of only corners reduces the amount of axial force required to operate the punch. This both enhances the longevity of the punch and requires a smaller machine to generate the punching force. Once the driving corners have been formed, the pilot hole is depetalled. This step is performed by inserting a tool bit sized to match the diameter of the pilot hole. The tool bit is used to remove the petals and any burrs created by the punching operation.

In the present invention the pilot hole and driving corners are formed by mechanical drilling and punching. However, it is contemplated that other methods of forming them could be used, such as, cold heading, hot heading, electrical discharge machining, electro chemical machining and any other known method for forming a socket with driving corners.

While the fastener illustrated with the preferred embodiment of the drive socket is intended for use in medical procedures, the unique drive socket configuration of the present invention may have applications in many others as well. In particular, the invention may be utilized in providing security type fasteners that may not be readily removed with conventional drivers. As will be appreciated, a standard hexagonal driver will have difficultly securely engaging the recessed drive corners and will likely ream out the socket before a sufficient torque can be applied.

Figure 4:
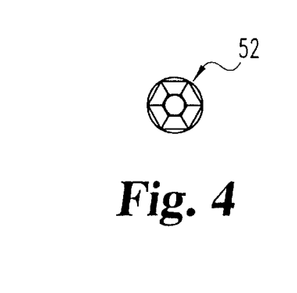
FIG. 4 is an end view of the driving tool of FIG. 3.

Referring now to FIGS. 3 through 6, a driving tool according to the present invention is illustrated. The driving tool illustrated is particularly adapted to drive relatively small fasteners similar to that shown in FIG. 2. However, it is contemplated that the driver can be sized or configured to fit a variety of socket sizes in various applications. Driving tool 50 includes a shaft 56, an engagement end 54 and a driving head 52. As shown in FIG. 4, driving head 52 is substantially hexagonally shaped so that the head roughly matches driving socket 13 of screw 10.

Figure 5:
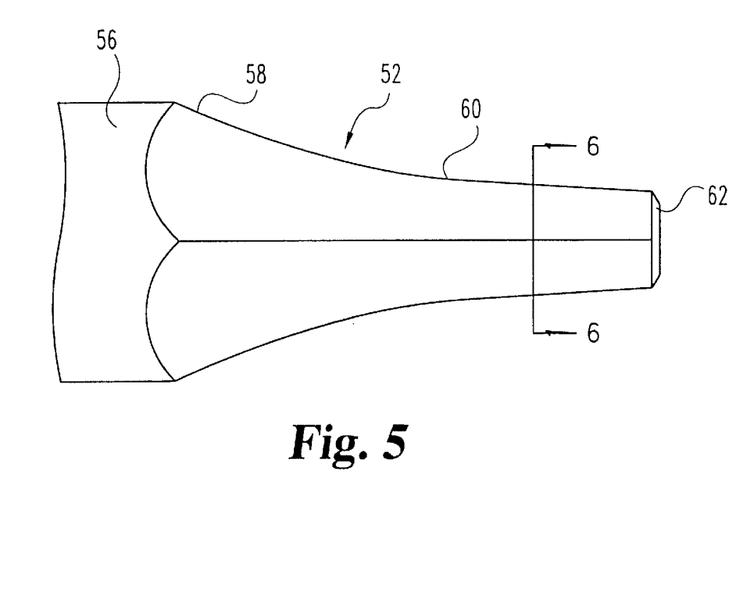
FIG. 5 is an enlarged view of the driving end of the driving tool of FIG. 3.
Figure 6:
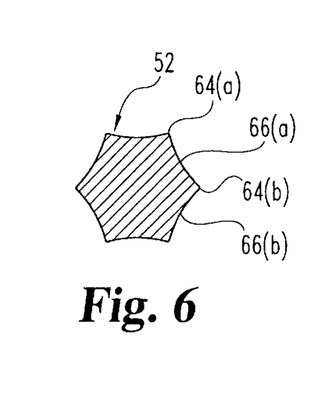
FIG. 6 is a cross-sectional view taken along section line 6—6 of the driving tool of FIG. 3.

Referring now to FIG. 5, driving head 52 has an enlarged diameter portion 58 adjacent shaft 56 and tapers rather sharply to a gradually tapering portion 60 continuing to taper to a reduced diameter adjacent chamfered tip 62. As shown in FIG. 6, driving head 52 includes six relatively sharp driving edges 64 formed at the junction of each of the six sides. Each driving edge 64 is separated from adjacent driving edges by a recess 66. In the preferred embodiment, concave recesses 66(a) and 66(b) cooperate to form a relatively sharp driving edge 64(b). Each of the remaining driving edges of the preferred embodiment are formed in a similar fashion. While smooth concave surfaces are utilized in the preferred embodiment, it is contemplated that other types of recesses could be used so long as a driving edge is formed at the junction between adjacent sides.

The driving head 52 of the driver according to the present invention is formed into a tapering hexagon in a conventional fashion. In the preferred method, a convex grinding wheel is applied between the junction of each side of the hexagonal driving end to form concave recesses 66 between each of the driving edges 64.

Figure 7:
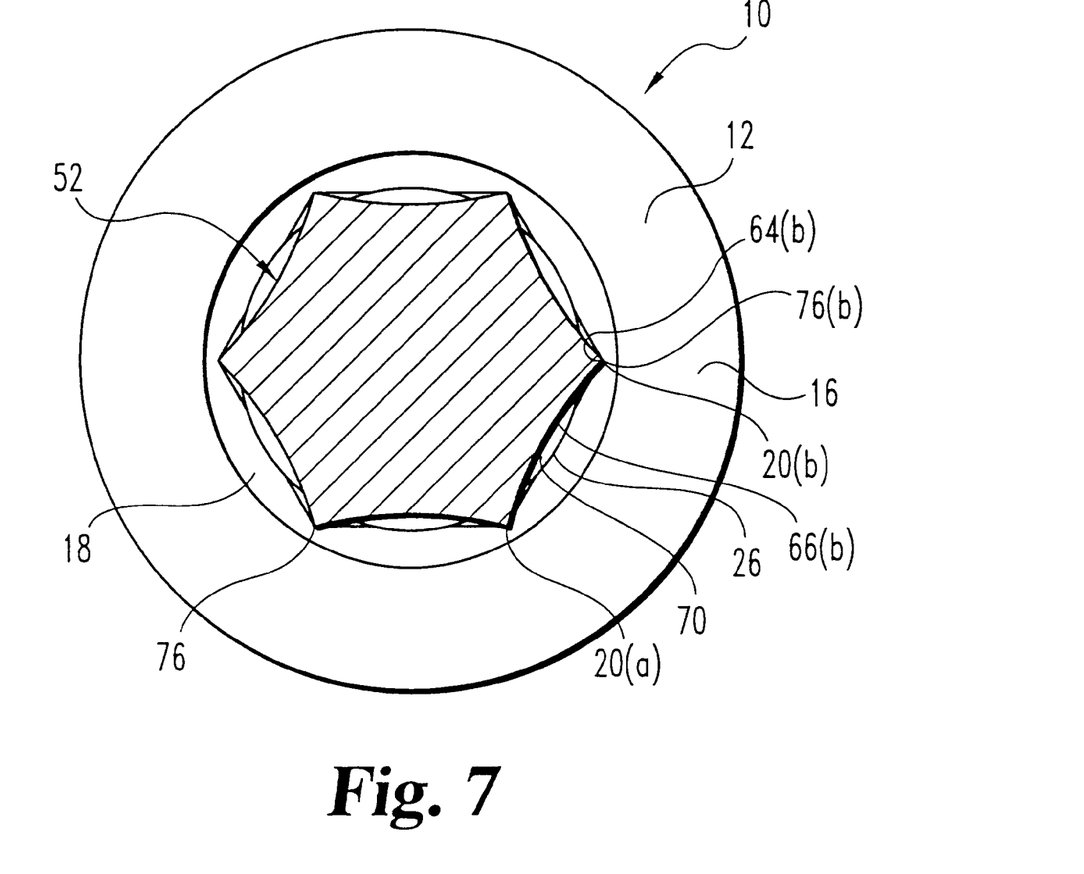
FIG. 7 is a top view of the recessed drive fastener of FIG. 1 with the cross-sectional view according to FIG. 6 disposed therein.
Figure 9:
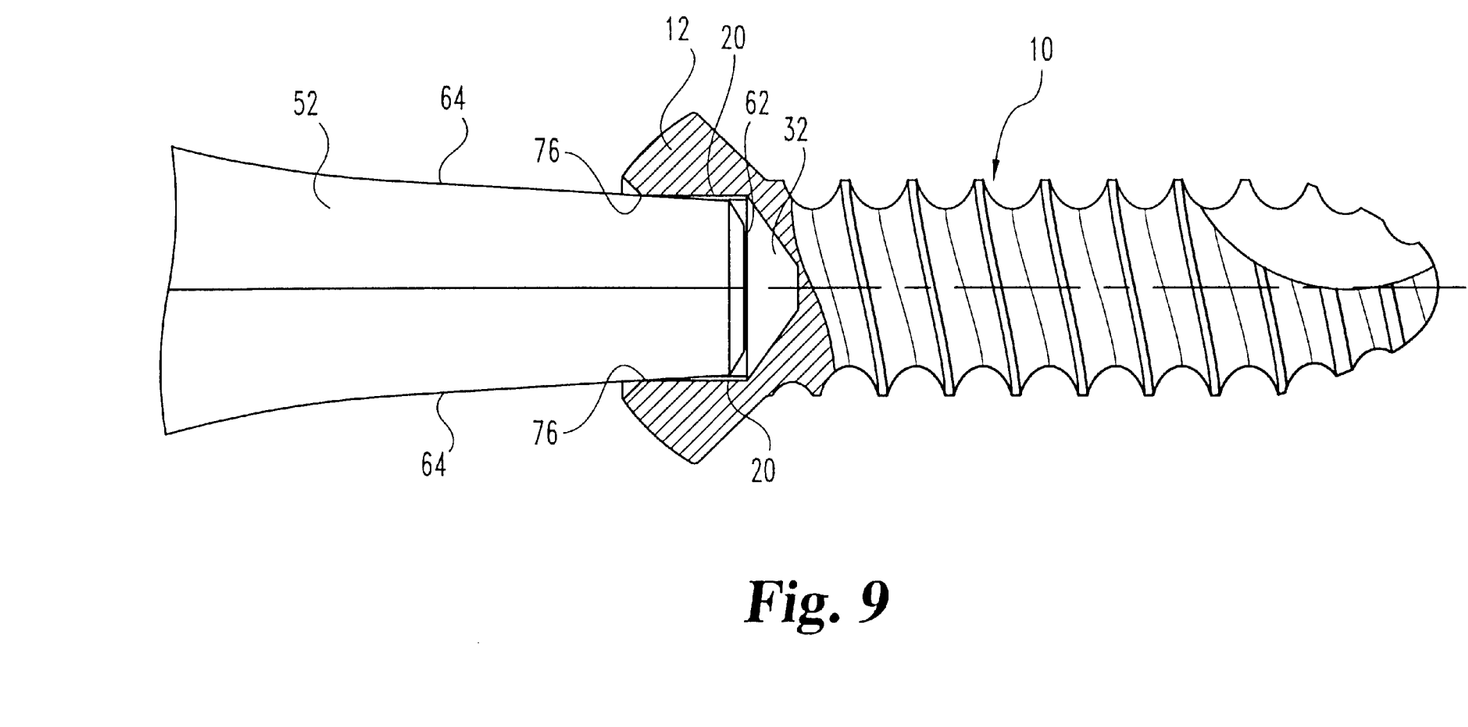
FIG. 9 is an enlarged detail of the driver head engaged with the drive socket.

Referring now to FIG. 7, in operation, driving head 52 of driving tool 50 is inserted into drive socket 13. Driving edges 64 are aligned with and positioned in driving corners 20. In the preferred embodiment driving head 52 is tapered as it extends towards its distal end 62. Thus, it may be axially moved into drive socket 13 until driving edges 64 abuttingly engage driving corners 20 at a contact point 76 along the tapering driving edges. As shown in FIG. 9, engagement of driving edges 64 with driving corners 20 at contact points 76, prevents tip 62 from reaching bottom wall 32.

The action of axially forcing driving end 52 into socket 13 generates a frictional engagement between driving tool 50 and fastener 10, such that fastener 10 is securely held on driving end 52. It will be understood that such a frictional engagement inhibits accidental removal of the driving tool when torque is being applied to screw 10. As a result of the tapering driving end, the engagement between driving edges 64 and driving corners 20 is isolated to a relatively small contact point 76 where the diameter of the driving edges equals the diameter of the driving corners. As will be appreciated by observing the tapering substantially hexagonal configuration, force applied against contact point 76(b) between driving edge 64(b) and driving corner 20(b) creates a similar force at the contact point between the diametrically opposed driving edge and driving corner. Thus, the essentially hexagonally shaped driving head 52 is securely wedged into the driving corners with each driving edge securely seated in the respective corners.

Although the wedged engagement of the driving head and socket securely holds the fastener on the driving tool and resists axial forces, the driving tool may also be easily removed. As shown in FIG. 9, the tapered driving head results in relatively small contact points 76 between the driving edges and the driving corners. This engagement permits the distal end of the driving head to move within the socket. Thus, the driving tool may be rocked side to side pivoting about these contact points 76, thereby loosening the frictional engagement between the driver and drive socket and permitting withdrawal of the driver from the fastener without undue axial force.

As shown in FIG. 7, with driving head 52 engaged in driving socket 13, recessed surfaces 66 between driving edges 64 are disposed opposite concave surfaces 26. This arrangement creates a fluid channel 70 which permits fluid disposed within driving socket 13 to be expelled upon insertion of driving head 52. Additionally, fluid channel 70 permits movement of fluid into socket 13 upon removal of driving tool 50 thus inhibiting a strong suction action tending to prevent removal of the driving head. In applications in which the screw is relatively small, such as for delicate orthopedic surgeries, this fluid channel prevents fluid from being trapped between the drive end and the socket which can generate sufficient hydraulic forces to inhibit axial movement of the driver with respect to the fastener.

The preferred embodiment of the present invention utilizes a concave surface in both the recessed socket and the corresponding recessed surfaced on the driving tool, however, it is contemplated that either the driving tool or the socket separately could define fluid channel 70. Moreover, although a plurality of fluid channels are shown in the present invention, it is contemplated that fewer fluid channels could be utilized. The size, shape and number of the channels utilized will depend on the application and environment in which the invention will be utilized, including in particular, the viscosity of the fluid expected to be present within drive socket 13.

Figure 8A:
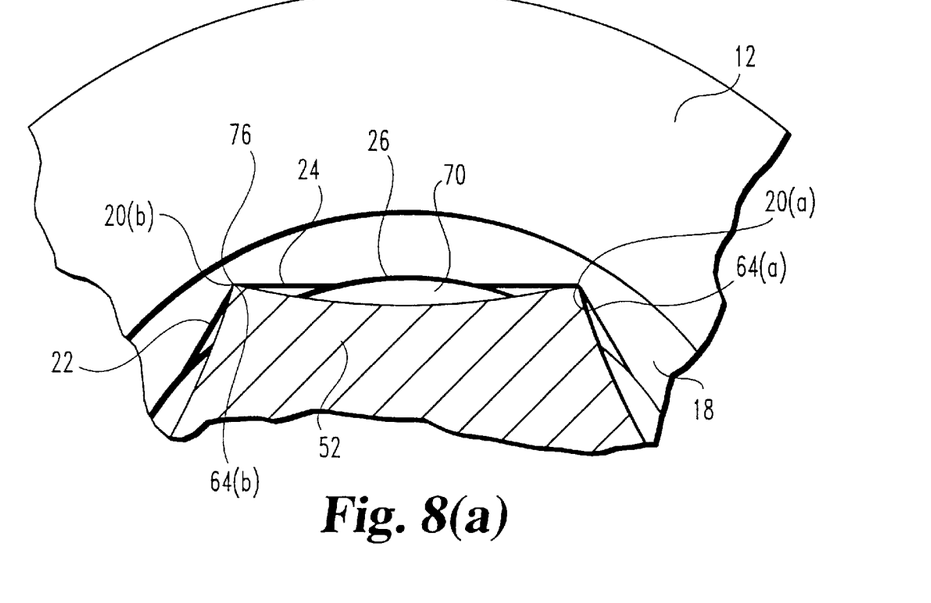
Figure 8B:
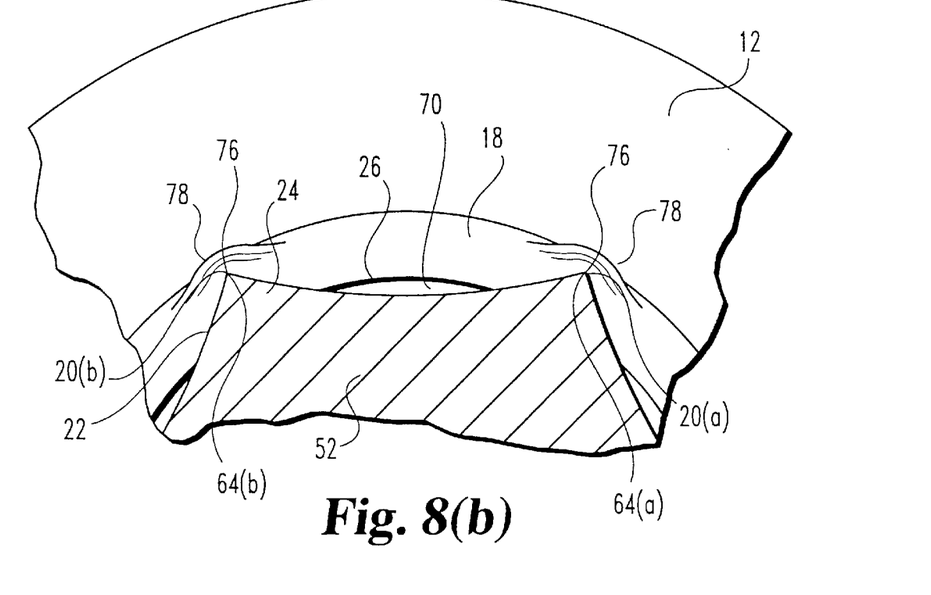

In addition to the geometric configuration of the drive socket and tapered driver, the preferred embodiment of the present invention utilizes a substantial difference in the material hardness between a relatively hard driver and a much softer drive socket to generate additional frictional engagement and improved torque transmission characteristics. During insertion, the driver is inserted into the socket until driving edges 64 abuttingly engage driving corners 20 (FIG. 8(a)). As more axial force is applied to the driver, the tapered driving head is urged further into the driving socket. The wedging action of the tapered driving head forces each driving edge 64 against the contact point 76 with the corresponding driving corner 20. Because of the difference in material hardness, the force applied to the driving edges results in deformation 78 (FIG. 8(b)) of the material at the corner. This deformation increases the frictional engagement between the driver and the socket thereby enhancing the driveability of the fastener (i.e. reducing wobble and inadvertent disengagement). Additionally, deformation of the material may work harden the corner resulting in enhanced mechanical properties over the non-deformed material.

In the preferred embodiment, the driver is preferrably constructed of 17-4 PH stainless steel heat treated to approximately a Rockwell C 45/47 hardness. The drive socket is formed of Ti6Al4V ELI titanium alloy, much softer than hardened stainless steel. The titanium alloy is accepted by ASTM as implant grade fastener material and is particularly useful in medical applications. Although metallic materials are utilized in the preferred embodiment, it is contemplated that other materials, including plastics and composite materials, could be utilized to form either the driver or the socket.

In addition to work hardening of the titanium alloy by deformation at the corner, insertion of the hardened driver galls the titanium leaving minute particles of the titanium bonded to the driver. After several uses, a thin titanium coating may be deposited on the driving edges. This titanium coating tends to increase the frictional engagement between the driving edges and the driving corners as a result of the titanium coating more effectively engaging the titanium corner. Additionally, the thin titanium coating inhibits minute particles of the stainless steel from being dislodged and adhering to the titanium drive socket. This is advantageous since the combination of steel and titanium creates a corrosive reaction when immersed in body fluids. Thus, it is desirable to limit the amount of stainless steel transferred to the titanium implant.

Not only does the corner-edge contact produce strong engagement forces, it also enhances the wear characteristics of the driving edges. As will be appreciated by those skilled in the art, wear of the driving edge will occur along the longitudinal driving edge as the driver is urged into the socket. Unlike many prior art devices, this wear is transverse with respect to the direction of rotational force applied by the driving edges on the socket driving corners. In the preferred embodiment, the wearing of tapered driving head 52 allows the driver to extend further into a similarly sized socket with a previously non-engaged portion of the driving head engaging the socket driving corners. Moreover, the wear resistance of the driver may be enhanced by a TIN (titanium nitride) coating. Such a coating is available from Multi-Arc, Inc. under the tradename ION BOND.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bone screw for attaching an implant to a bone portion, the bone screw comprising a head adapted to engage an implant and a threaded shaft configured for engaging the bone portion, wherein the head includes a recessed drive socket for receiving a partially mating, rotational drive tool therein, wherein the socket comprises a socket cavity having a generally cylindrical wall having a longitudinal length, said cylindrical wall substantially smooth throughout said longitudinal length and interrupted by a plurality of pre-formed driving corners formed by a pair of substantially planar surfaces joined at a junction, each surface abutting the cylindrical wall, wherein said driving corners receive a portion of the driver tool therein.

2. The bone screw of claim 1, wherein said plurality of driving corners are spaced equidistant around said cylindrical wall.

3. The bone screw of claim 1, wherein each of said plurality of driving corners is a recessed area in said cylindrical wall.

4. The bone screw of claim 1, wherein said series of driving corners includes six equally spaced recesses defined in said cylindrical wall.

5. A bone screw and driver combination, comprising:
a bone screw having a drive socket, said socket having a substantially cylindrical wall having a longitudinal length, said wall substantially smooth throughout said longitudinal length, and a plurality of pre-formed driving corners formed by a pair of substantially planar surfaces joined at a junction, each surface abutting the cylindrical wall; and
a driver having a driving head including a plurality of driving edges sized for mating engagement with corresponding driving corners of said bone screw, said driving head further defining a recessed area between each driving edge.

6. The bone screw and driver combination of claim 5, wherein said driving head has an external diameter, a proximal portion and a distal tip, said external diameter tapering between a first diameter adjacent said proximal portion and a second diameter adjacent said distal tip, said first diameter being larger than said second diameter, wherein upon insertion of said driver head into said recessed drive socket said driving head may be advanced until a portion of said driving edges having a third diameter intermediate said first and second diameters abuttingly engage said driving corners.

7. The bone screw and driver combination of claim 6, wherein said driver is made of a first material and said fastener is made of a second material, said first material being harder than said second material, and wherein further axial movement of said driver into said fastener after abutting engagement results in a deformation of said driving corners, said deformation enhancing frictional engagement of said driver in said fastener.

8. The bone screw and driver combination of claim 7, wherein said first material is heat treated stainless steel and said second material is a titanium alloy, wherein deformation of said titanium alloy work hardens the material resulting in greater mechanical strength.

9. A bone screw and driver combination, comprising:
   a bone screw having a recessed drive socket, said socket defined by a substantially cylindrical interior wall having a longitudinal length, said interior wall substantially smooth throughout said longitudinal length and interrupted by a plurality of driving corners formed by a pair of substantially planar surfaces joined at a junction, each surface abutting the cylindrical interior wall,
   a driver having a driving head including an outer surface defining a plurality of driving edges spaced for mating engagement with the corresponding driving corners of said bone screw, said cylindrical interior wall of said bone screw and said outer surface of said driver define at least one fluid channel, said fluid channel permitting the passage of fluid during movement of said driver with respect to said recessed drive socket.

10. The bone screw of claim 1 wherein the threaded shaft has an outer diameter of about 1.0 mm to about 5.0 mm.

11. The bone screw and driver combination of claim 5 wherein the bone screw has an outer thread diameter of about 1.0 mm to about 5.0 mm.

12. The bone screw of claim 1 wherein the driving corners are spaced apart by a plurality of concave surfaces.

13. The bone screw of claim 1 wherein the bone screw includes a longitudinal axis and the driving corners extend longitudinally essentially parallel to the longitudinal axis of the bone screw.

14. The bone screw and driver combination of claim 9 wherein the fluid channel permits passage of bodily fluids.

15. The bone screw and driver combination of claim 9 wherein the fluid channel is sized to inhibit hydraulic lock of the driver by bodily fluids.

16. The bone screw of claim 9 wherein the bone screw includes a longitudinal axis and the driving corners extend longitudinally essentially parallel to the longitudinal axis of the screw.

17. A bone screw and driver combination, comprising:
   a bone screw having a recessed drive socket, said socket defined by a plurality of driving corners formed by a pair of substantially planar surfaces joined at a junction, each of said driving corners separated from an adjacent driving corner by a concave surface having a longitudinal length, said concave surface substantially smooth throughout said longitudinal length, each substantially planar surface abutting a concave surface; and
   a driver having a driving head including an outer surface defining a plurality of driving edges spaced apart by a plurality of recessed surfaces, wherein the driving edges are provided for mating engagement with the driving corners of said bone screw and the recessed surfaces are adapted to prevent complete engagement of said driving head with said concave surface.

18. The bone screw and driver combination of claim 17 wherein upon engagement of said driving edges with said driving corners, portions of said concave surfaces and said recessed surfaces define a plurality of fluid channels to permit passage of bodily fluids from the recessed drive socket when the driving edges engage the driving corners.

19. The bone screw and driver combination of claim 17 wherein said concave surfaces are cylindrical wall portions.

20. The bone screw and driver combination of claim 19 wherein the recessed surfaces are positioned opposite the cylindrical wall portions when the driving edges matingly engage the driving corners.

21. A bone screw for attaching an implant to a bone portion, the bone screw comprising:
   a threaded shaft configured for engaging the bone portion and having an outer thread diameter of between about 1.0 mm and about 5.0 mm; and
   a head adapted to engage an implant, wherein the head includes a recessed drive socket for receiving a partially mating, rotational drive tool therein, the socket comprising a socket cavity having a generally cylindrical wall having a longitudinal length, said cylindrical wall substantially smooth throughout said longitudinal length and interrupted by a plurality of preformed driving corners formed by the junction of a pair of substantially planar surfaces each surface abutting the cylindrical wall, said driving corners spaced apart by a plurality of concave surfaces, wherein the concave surfaces are adapted to inhibit hydraulic lock by bodily fluids from inducing bone screw pullout upon disengagement of the drive tool from the recessed socket.

* * * * *

UNITED STATES PATENT AND TRADEMARK OFFICE
CERTIFICATE OF CORRECTION

PATENT NO. : 6,016,727  
DATED : January 25, 2000  
INVENTOR(S) : Morgan

Page 1 of 1

It is certified that error appears in the above-identified patent and that said Letters Patent is hereby corrected as shown below:

<u>Title page,</u>  
References Cited, OTHER PUBLICATIONS,  
Please delete "vol." and insert in lieu thereof -- Vol. --.

<u>Column 1,</u>  
Line 7, please delete the second occurrence of "application" and insert in lieu thereof -- Application --.

<u>Column 2,</u>  
Line 24, please delete "were" and insert in lieu thereof -- where --.

<u>Column 9,</u>  
Line 46, please delete "comers" and insert in lieu thereof -- corners --.

Signed and Sealed this

Twenty-sixth Day of February, 2002

*Attest:*

*Attesting Officer*

JAMES E. ROGAN  
*Director of the United States Patent and Trademark Office*